United States Patent
O'Shaughnessy et al.

(10) Patent No.: US 10,117,761 B2
(45) Date of Patent: Nov. 6, 2018

(54) STENT WITH ANTI-MIGRATION FEATURES

(71) Applicant: BOSTON SCIENTIFIC SCIMED, INC., Maple Grove, MN (US)

(72) Inventors: Seamus F. O'Shaughnessy, Chelmsford, MA (US); Gary J. Leanna, Holden, MA (US); Jason Weiner, Grafton, MA (US); Dane T. Seddon, Boston, MA (US); Sean P. Fleury, Brighton, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 14/974,069

(22) Filed: Dec. 18, 2015

(65) Prior Publication Data

US 2016/0175122 A1    Jun. 23, 2016

Related U.S. Application Data

(60) Provisional application No. 62/094,216, filed on Dec. 19, 2014.

(51) Int. Cl.
*A61F 2/848* (2013.01)
*B21C 37/06* (2006.01)
(Continued)

(52) U.S. Cl.
CPC ........... *A61F 2/848* (2013.01); *A61F 2/04* (2013.01); *A61F 2/86* (2013.01); *A61F 2/92* (2013.01); *B21C 37/065* (2013.01); *A61F 2/91* (2013.01); *A61F 2002/0081* (2013.01); *A61F 2002/825* (2013.01); *A61F 2002/8483* (2013.01);
(Continued)

(58) Field of Classification Search
CPC ...... A61F 2/04–2/06; A61F 2/848–2002/8486; A61F 2220/0008–2220/0016; A61F 2230/0069; A61F 2250/0025; A61F 2250/0026; B21C 37/065
See application file for complete search history.

(56) References Cited

U.S. PATENT DOCUMENTS

| 5,397,355 A | 3/1995 | Marin et al. |
| 5,421,955 A * | 6/1995 | Lau .......................... A61F 2/86 216/48 |

(Continued)

FOREIGN PATENT DOCUMENTS

| JP | 2007185363 A1 | 7/2007 |
| WO | 0100112 A1 | 1/2001 |

(Continued)

*Primary Examiner* — Paul Prebilic
(74) *Attorney, Agent, or Firm* — Seager, Tufte & Wickhem, LLP

(57) ABSTRACT

An endoprosthesis includes an expandable tubular framework having a first end, a second end, and a lumen extending therethrough along a longitudinal axis. The expandable tubular framework includes a plurality of interconnected struts. The interconnected struts include a radially outward face which includes a plurality of anti-migration grooves defining anti-migration teeth formed therebetween. The anti-migration teeth are configured to engage tissue to resist migration of the endoprosthesis within a body lumen.

20 Claims, 6 Drawing Sheets

(51) Int. Cl.
*A61F 2/04* (2013.01)
*A61F 2/86* (2013.01)
*A61F 2/92* (2013.01)
*A61F 2/82* (2013.01)
*A61F 2/91* (2013.01)
*A61F 2/00* (2006.01)

(52) U.S. Cl.
CPC ............... *A61F 2002/8486* (2013.01); *A61F 2220/0016* (2013.01); *A61F 2230/0023* (2013.01); *A61F 2240/001* (2013.01)

(56) References Cited

U.S. PATENT DOCUMENTS

| | | | |
|---|---|---|---|
| 9,855,129 B2* | 1/2018 | DeBruyne | A61F 2/07 |
| 9,855,155 B2* | 1/2018 | Majercak | A61F 2/852 |
| 2003/0093145 A1 | 5/2003 | Lawrence-Brown et al. | |
| 2003/0229389 A1* | 12/2003 | Escano | A61F 2/07 623/1.13 |
| 2005/0209684 A1 | 9/2005 | Alexander et al. | |
| 2006/0253190 A1 | 11/2006 | Kuo | |
| 2007/0032857 A1* | 2/2007 | Schmid | A61F 2/915 623/1.16 |
| 2008/0097591 A1* | 4/2008 | Savage | A61F 2/91 623/1.43 |
| 2010/0256742 A1 | 10/2010 | Kleine et al. | |
| 2011/0270405 A1* | 11/2011 | Geitz | A61F 2/90 623/23.7 |
| 2011/0276125 A1* | 11/2011 | Walker | A61F 2/915 623/1.15 |
| 2012/0035705 A1 | 2/2012 | Giasolli et al. | |
| 2012/0095545 A1* | 4/2012 | Yamagata | A61F 2/82 623/1.16 |
| 2013/0018215 A1 | 1/2013 | Snider et al. | |
| 2013/0018452 A1* | 1/2013 | Weitzner | A61F 2/848 623/1.15 |
| 2013/0172983 A1 | 7/2013 | Clerc et al. | |
| 2013/0268063 A1* | 10/2013 | Firstenberg | A61F 2/06 623/1.46 |
| 2014/0094929 A1 | 4/2014 | Shin et al. | |

FOREIGN PATENT DOCUMENTS

| | | |
|---|---|---|
| WO | 03037222 A2 | 5/2003 |
| WO | 2005086733 A2 | 9/2005 |

* cited by examiner

STENT WITH ANTI-MIGRATION FEATURES

CROSS-REFERENCE TO RELATED APPLICATIONS

This application claims priority under 35 U.S.C. § 119(e) to U.S. Provisional Application No. 62/094,216, filed Dec. 19, 2014, the entire disclosure of which is herein incorporated by reference.

TECHNICAL FIELD

The disclosure is directed to an endoprosthesis, such as a stent, including anti-migration features. More particularly, the disclosure is directed to an endoprosthesis, such as a stent, including a plurality of anti-migration teeth along a surface thereof.

BACKGROUND

An endoprosthesis may be configured to be positioned in a body lumen for a variety of medical applications. For example, an endoprosthesis may be used to treat a stenosis in a blood vessel, used to maintain a fluid opening or pathway in the vascular, urinary, biliary, tracheobronchial, esophageal or renal tracts, or to position a device such as an artificial valve or filter within a body lumen, in some instances. Bare or partially covered endoprostheses allow tissue ingrowth through the structure of the endoprosthesis to prevent migration of the endoprosthesis. However, if it is desired to remove the endoprosthesis at some later time, the ingrown tissue must be cut away, causing significant trauma to the body lumen. Fully covered endoprostheses, on the other hand, prevent tissue ingrowth to facilitate removal. However, fully covered endoprostheses are prone to migrate through the body lumen.

Accordingly, it is desirable to provide endoprostheses that exhibit anti-migration features, while reducing the trauma to the body lumen of the patient if removal of the endoprosthesis is desired.

BRIEF SUMMARY

The disclosure is directed to several alternative designs, materials and methods of manufacturing medical device structures and assemblies, and uses thereof.

In one example, an endoprosthesis comprises an expandable tubular framework having a first end, a second end, and a lumen extending therethrough along a longitudinal axis. The expandable tubular framework includes a plurality of interconnected struts. The interconnected struts include a radially outward face which includes a plurality of anti-migration grooves defining anti-migration teeth formed therebetween. The anti-migration teeth are configured to engage tissue to resist migration of the endoprosthesis within a body lumen.

Additionally or alternatively, each of the anti-migration teeth include a first flank and a second flank converging toward the first flank.

Additionally or alternatively, the first flank slopes radially outward toward the first end at an acute angle with respect to the longitudinal axis.

Additionally or alternatively, the second flank slopes radially outward toward the first end at an acute angle with respect to the longitudinal axis.

Additionally or alternatively, the angle of the first flank is less than the angle of the second flank.

Additionally or alternatively, the first flank and the second flank converge to a point along a line.

Additionally or alternatively, the anti-migration teeth further include a flat surface intersecting both the first flank and the second flank.

Additionally or alternatively, the flat surface is generally parallel to the longitudinal axis.

Additionally or alternatively, a first portion of the anti-migration teeth include at least one of the first and second flanks angled toward the first end, and a second portion of the anti-migration teeth include at least one of the first and second flanks angled toward the second end.

Additionally or alternatively, the first portion of the anti-migration teeth are located proximate the first end and the second portion of the anti-migration teeth are located proximate the second end.

Additionally or alternatively, the first portion of the anti-migration teeth are located proximate the second end and the second portion of the anti-migration teeth are located proximate the first end.

Additionally or alternatively, the expandable tubular framework is devoid of anti-migration teeth between the first portion of anti-migration teeth and the second portion of anti-migration teeth.

Additionally or alternatively, the anti-migration teeth are oriented generally perpendicular to the longitudinal axis.

Additionally or alternatively, the anti-migration teeth are oriented at an oblique angle to the longitudinal axis.

Additionally or alternatively, the anti-migration grooves extend into the struts to a depth of about 1% to about 10% of a thickness of the struts.

In another example, an endoprosthesis comprises an expandable tubular framework having a first end, a second end, and a lumen extending therethrough along a longitudinal axis. The expandable tubular framework includes a plurality of interconnected struts which include a radially outward surface. The radially outward surface includes a plurality of anti-migration grooves cut into the radially outward surface of the interconnected struts to define anti-migration teeth formed therebetween. The anti-migration teeth include a first flank and a second flank converging toward the first flank. The anti-migration teeth are configured to engage tissue to resist migration of the endoprosthesis within a body lumen.

Additionally or alternatively, a first portion of the anti-migration teeth include at least one of the first and second flanks angled toward the first end, and a second portion of the anti-migration teeth include at least one of the first and second flanks angled toward the second end.

Additionally or alternatively, the first flank slopes radially outward toward the first end at an acute angle with respect to the longitudinal axis.

Additionally or alternatively, the second flank slopes radially outward toward the first end at an acute angle with respect to the longitudinal axis.

Additionally or alternatively, the angle of the first flank is less than the angle of the second flank.

Additionally or alternatively, the anti-migration teeth further include a flat surface intersecting both the first flank and the second flank.

Another example is a method of forming an endoprosthesis. The method includes forming an expandable tubular framework from a tubular member. The expandable tubular framework has a first end, a second end, and a lumen extending therethrough along a longitudinal axis. The expandable tubular framework includes a plurality of interconnected struts having a radially outward facing surface.

The method further includes forming a plurality of anti-migration grooves in the radially outward facing surface, thereby defining a plurality of anti-migration teeth between adjacent anti-migration grooves.

Additionally or alternatively, the anti-migration teeth include a first flank and a second flank converging toward the first flank. The first flank slopes radially outward toward the first end at an acute angle from the longitudinal axis and the second flank slopes radially outward toward the first end at an acute angle from the longitudinal axis. The angle of the first flank is less than the angle of the second flank.

Additionally or alternatively, the anti-migration teeth further include a flat surface intersecting both the first flank and the second flank.

The above summary of some example embodiments is not intended to describe each disclosed embodiment or every implementation of the aspects of the disclosure.

BRIEF DESCRIPTION OF THE DRAWINGS

The aspects of the disclosure may be further understood in consideration of the following detailed description of various embodiments in connection with the accompanying drawings, in which.

Figure 1:
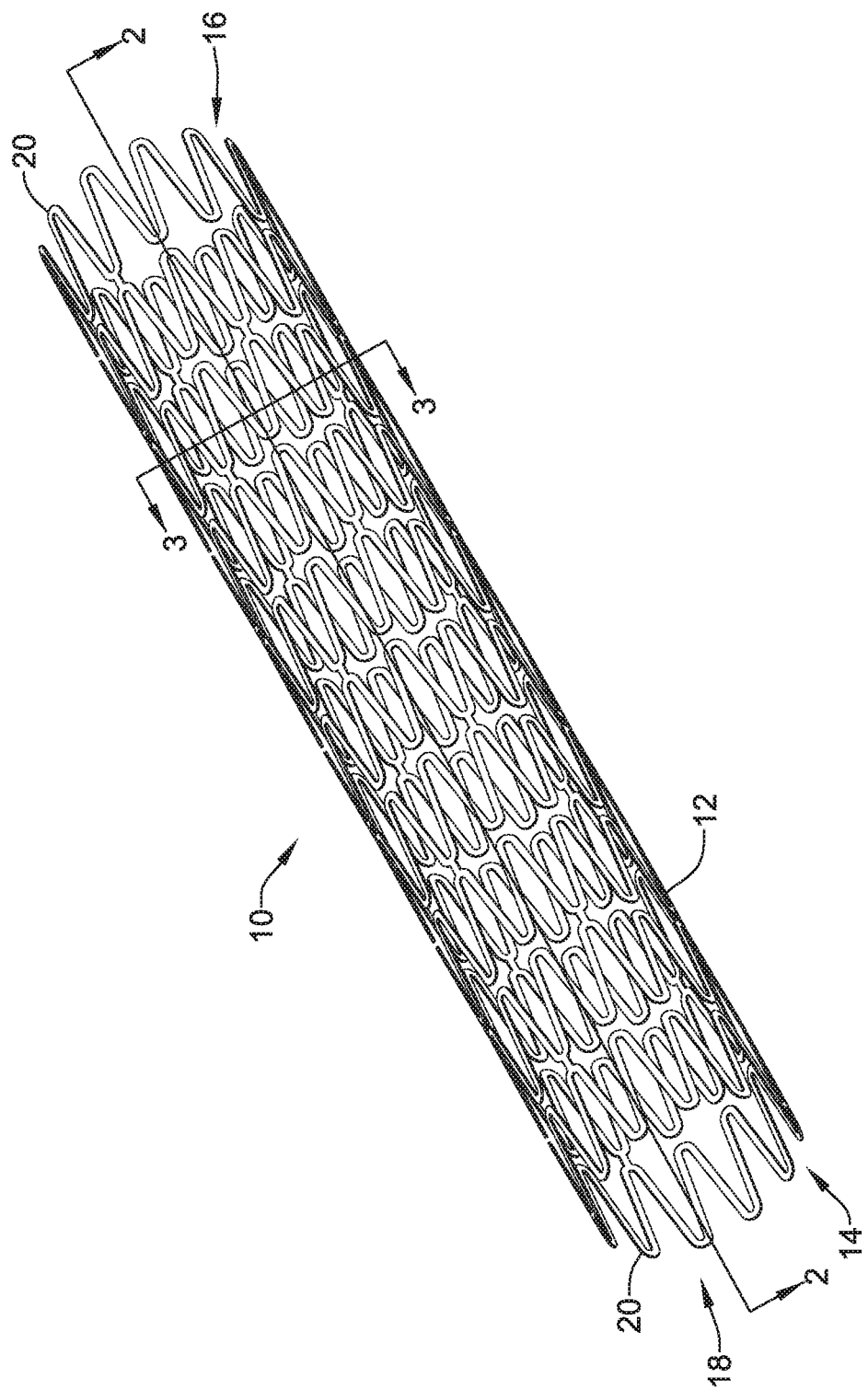
FIG. 1 is a perspective view of an exemplary endoprosthesis.

While the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

Definitions of certain terms are provided below and shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

FIG. 1 illustrates an exemplary endoprosthesis 10. The endoprosthesis 10 may be configured to be positioned in a body lumen for a variety of medical applications. For example, the endoprosthesis 10 may be used to treat a stenosis in a blood vessel, used to maintain a fluid opening or pathway in the vascular, urinary, biliary, tracheobronchial, esophageal or renal tracts, or position a device such as an artificial valve or filter within a body lumen, in some instances. In some instances, the endoprosthesis 10 may be a prosthetic graft, a stent-graft, or a stent (e.g., a vascular stent, tracheal stent, bronchial stent, esophageal stent, etc.), an aortic valve, filter, etc. Although illustrated as a stent, the endoprosthesis 10 may be any of a number of devices that may be introduced endoscopically, subcutaneously, percutaneously or surgically to be positioned within an organ, tissue, or lumen, such as a heart, artery, vein, urethra, esophagus, trachea, bronchus, bile duct, or the like.

The endoprosthesis 10 may include a first end 14, a second end 16, and an expandable tubular framework 12 disposed about a longitudinal axis of the endoprosthesis 10 that defines a lumen 18 extending therethrough. The term 'expandable tubular framework 12' may be referred to as 'expandable framework 12' hereafter. The expandable framework 12 may include a number of interconnected struts 20 to form a mesh-like structure of the expandable framework 12. The struts 20 may be configured to transition from a compressed state to an expanded state.

The endoprosthesis 10 may be configured to be implanted in the vasculature of a patient, such as an aortic ostium, tortuous vessels, etc. In other embodiments, the endoprosthesis 10 may be configured to be implanted in the urinary, biliary, tracheobronchial, esophageal or renal tracts, for example. The endoprosthesis 10, or a portion thereof, may be made from a biostable material, a bioabsorbable material, or a combination thereof. Examples of the biostable metal materials may include, but are not limited to, stainless steel, tantalum, tungsten, niobium, platinum, nickel-chromium alloys, cobalt-chromium alloys such as Elgiloy® and Phynox®, nitinol (e.g., 55% nickel, 45% titanium), and other alloys based on titanium, including nickel titanium alloys, or other suitable metals, or combinations or alloys thereof. Some suitable biostable polymeric materials include, but are not necessarily limited to, polyamide, polyether block amide, polyethylene, polyethylene terephthalate, polypropylene, polyvinylchloride, polyurethane, polytetrafluoroethylene, polysulfone, and copolymers, blends, mixtures or combinations thereof. Examples of suitable bioabsorbable materials may include polymers, such as poly-L-lactide (PLLA), polyglycolide (PGA), poly-lactide (PLA), poly-D-lactide (PDLA), polycaprolactone, polydioxanone, polygluconate, polylactic acid-polyethylene oxide copolymers, modified cellulose, collagen, poly(hydroxybutyrate), polyanhydride, polyphosphoester, poly(amino acids), and combinations thereof.

Figure 2:
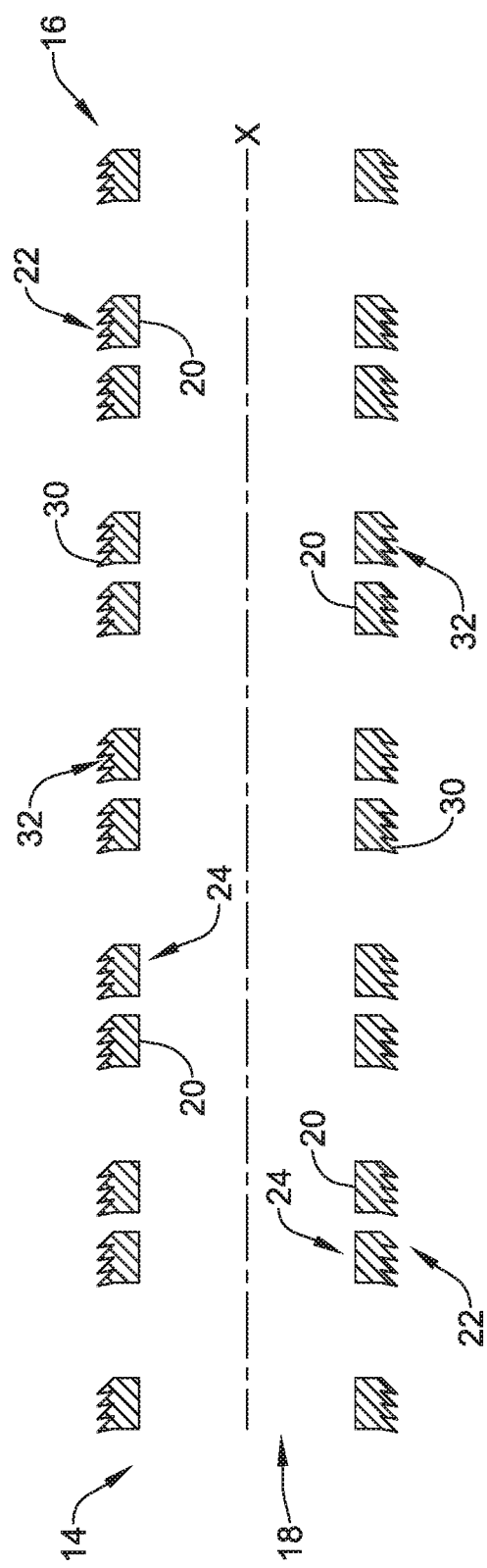
FIG. 2 is a longitudinal cross-section of the endoprosthesis of FIG. 1 taken along line 2-2.
Figure 3:
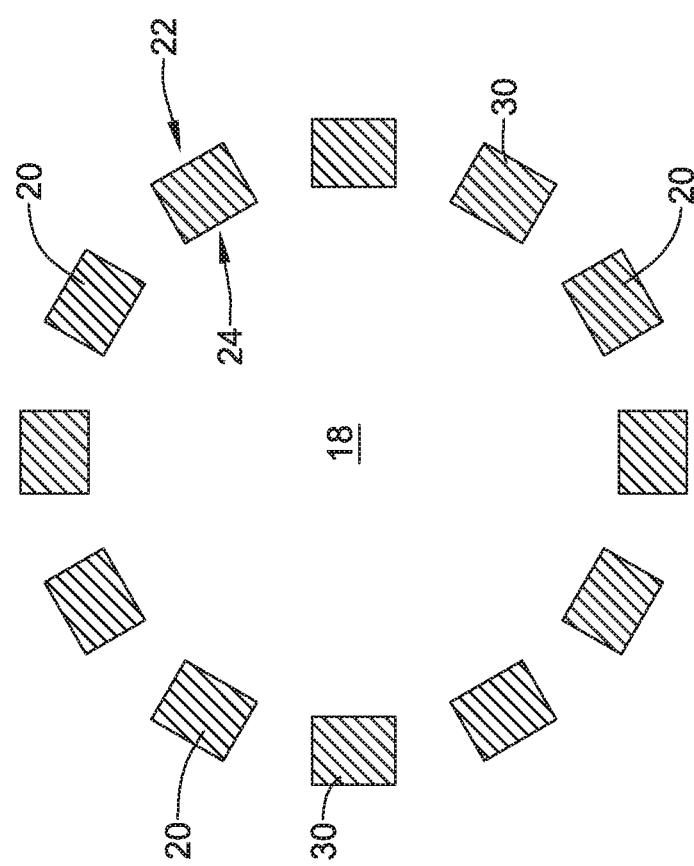
FIG. 3 is a transverse cross-section of the endoprosthesis of FIG. 1 taken along line 3-3.

Referring to FIGS. 2 and 3, the interconnected struts 20 may include a radially outward face 22 around the outer periphery of the expandable framework 12 and an opposite radially inward face 24 facing the lumen 18 extending through the expandable framework 12. As shown in FIG. 2, the radially outward face 22 may include a plurality of anti-migration grooves 32 defining anti-migration teeth 30 formed therebetween. The anti-migration teeth 30 may be configured to engage tissue to resist migration of the endoprosthesis 10 when implanted in a body lumen.

The anti-migration teeth 30 may be formed along any desired region of the radially outward face 22 of the expandable framework 12. For example, the anti-migration teeth 30 may be formed along substantially all of the radially outward face 22, or along any desired portion thereof. In some instances, the anti-migration teeth 30 may be present in discrete regions of the radially outward face 22 of the expandable framework 12 while the remainder of the radially outward face 22 of the expandable framework 12 remains devoid of anti-migration teeth 30. For example, in some instances the anti-migration teeth 30 may be present in discrete circumferential rings around the circumference of the expandable framework 12 and/or the anti-migration teeth 30 may be present in discrete longitudinal strips along the longitudinal axis X of the expandable framework 12. It is noted that the anti-migration teeth 30 may be present in other discrete patterns on the radially outward face 22, if desired.

Figure 4:
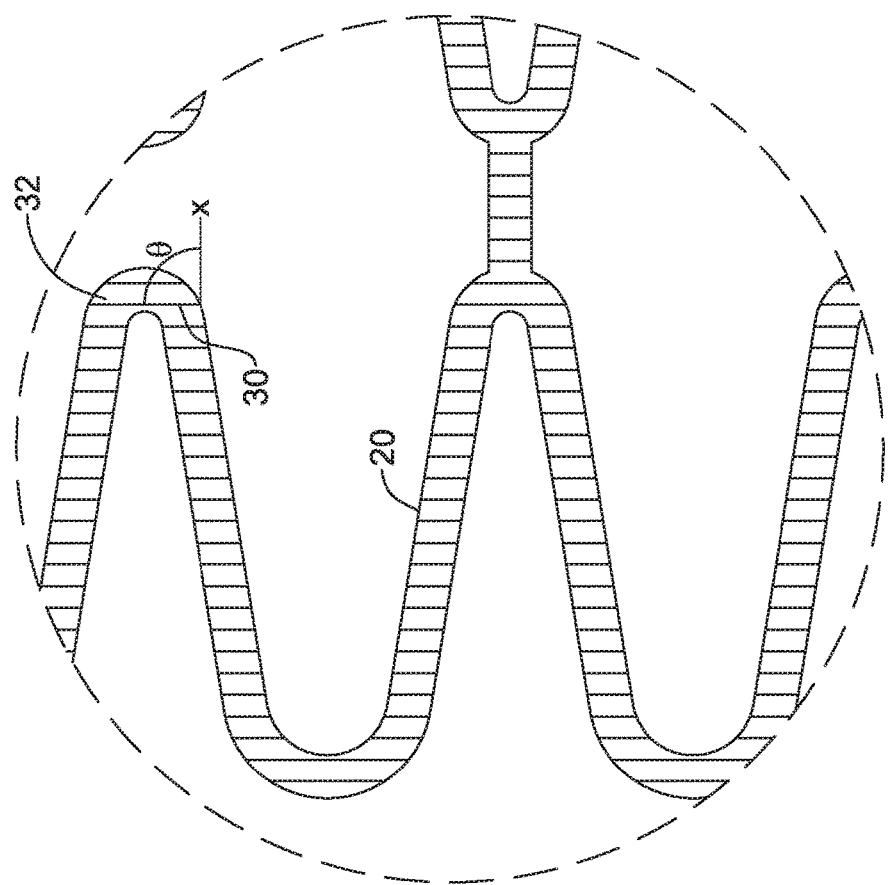
FIG. 4 is an enlarged view of a portion of the expandable framework of the endoprosthesis of FIG. 1.

The anti-migration teeth 30 may be oriented in any desired orientation on the radially outward face 22. For example, in some instances the anti-migration teeth 30 may be oriented in parallel rows of anti-migration teeth 30 with anti-migration grooves 32 located therebetween. The rows of anti-migration teeth 30 may be oriented at any desired angle $\theta$ relative to the longitudinal axis X of the expandable framework 12. In other words, the longitudinal extensions of the anti-migration teeth 30 along the outward face 22 may be oriented parallel to one another at any desired angle to the longitudinal axis of the X of the expandable framework 12. For example, as shown in FIG. 4 the rows of anti-migration teeth 30 may be oriented generally perpendicular to the longitudinal axis X of the expandable framework 12 such that the angle $\theta$ is 90° or approximately 90°, such as between 88° to 92°. In other instances, the rows of anti-migration teeth 30 may be oriented generally parallel to the longitudinal axis X of the expandable framework 12 such that the angle $\theta$ is 0° or approximately 0°, such as less than 3° or less than 2°. In yet other instances, the rows of anti-migration teeth 30 may be oriented at an oblique angle to the longitudinal axis X. In some such instances, the angle $\theta$ may be in the range of 5° to 85°, or about 5° to about 85°, 10° to 80°, or about 10° to about 80°, 15° to 75°, or about 15° to about 75°, 30° to 60°, or about 30° to about 60°, 5° to 60°, or about 5° to about 60°, or 45° to 85°, or about 45° to about 85°, for example. In some instances the angle $\theta$ may be 5°, 10°, 15°, 20°, 30°, 45°, 60°, 75°, 80° or 85°, or about 5°, 10°, 15°, 20°, 30°, 45°, 60°, 75°, 80° or 85°, for example.

The anti-migration teeth 30 may be formed in the radially outward face 22 of the expandable framework 12 in any desired way. For example, the anti-migration teeth 30 may be formed by creating the anti-migration grooves 32 during a laser cutting process, chemical etching process, a micromachining process, or other process, such as another process in which material of the expandable framework 12 is removed to form the anti-migration grooves 32 defining the anti-migration teeth 32 therebetween. In a laser cutting process, for example, the laser may be positioned at an acute angle to the longitudinal axis X of the expandable framework 12 such that the anti-migration teeth 30 will be formed at an acute angle to the longitudinal axis X. It is noted that the anti-migration grooves 32 defining the anti-migration teeth 30 may be formed in the tubular member prior to removing material of the tubular member to form the interconnected struts 20. In other words, the tubular member, such as a metallic tubular member (e.g., nitinol hypotube) may be subjected to a first laser cutting process to form the anti-migration grooves 32 defining the anti-migration teeth 30 on the outer surface of the tubular member, and the interconnected struts 20 may be formed in the tubular member (by removing material of the tubular member between adjacent struts 20) during a subsequent laser cutting process. In other instances, the anti-migration grooves 32 defining the anti-migration teeth 30 may be formed in the tubular framework 12 subsequent to removing material from the tubular member to form the interconnected struts 20.

FIGS. 5A-5D illustrate some exemplary configurations of anti-migration teeth 30 formed on the radially outward face 22 of the interconnected struts 20 of the expandable framework 12. The anti-migration teeth 30 may include a first flank 34 and a second flank 36 converging toward the first flank 34.

The first flank 34 may extend at an angle $\alpha$ relative to the longitudinal axis X of the tubular framework 12. The angle $\alpha$ may be any desired angle, such as an acute angle. In some instances, the angle $\alpha$ may be in the range of 45° to 80°, or about 45° to about 80°, 45° to 75°, or about 45° to about 75°, 45° to 70°, or about 45° to about 70°, 60° to 80°, or about 60° to about 80°, or 60° to 70°, or about 60° to about 70°.

The second flank 36 may extend at an angle $\beta$ relative to the longitudinal axis X of the tubular framework 12. The angle $\beta$ may be any desired angle, such as an acute angle (i.e., an angle $\beta$ less than 90°), a perpendicular angle (i.e., an angle $\beta$ equal to 90°), or an obtuse angle (i.e., an angle $\beta$ greater than 90°). In some instances, the angle $\beta$ may be in the range of 60° to 135°, or about 60° to about 135°, 60° to 120°, or about 60° to about 120°, 60° to 100°, or about 60° to about 100°, 60° to 90°, or about 60° to about 90°, 60° to 85°, or about 60° to about 85°, 60° to 80°, or about 60° to about 80°, 60° to 75°, or about 60° to about 75°, or 60° to 70°, or about 60° to about 70°.

The angle $\alpha$ of the first flank 34 may be less than the angle $\beta$ of the second flank 36. For example, the first flank 34 may have an acute angle falling within the ranges provided above while the second flank 36 may have an angle $\beta$ falling within the ranges provided above and is greater than the angle $\alpha$ of the first flank 34.

Figure 5A:
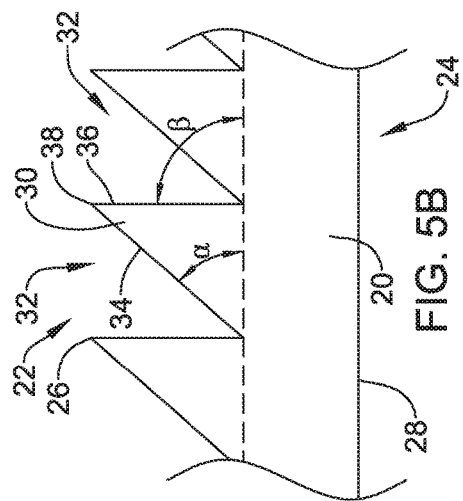
FIGS. 5A-5D illustrate some exemplary configurations of anti-migration teeth formed on the expandable framework of the endoprosthesis of FIG. 1.

As shown in FIG. 5A, in some instances both the angle $\alpha$ of the first flank 34 and the angle $\beta$ of the second flank 36 may be acute angles such that both the first flank 34 and the second flank 36 slope radially outward from the longitudinal axis toward the same end (e.g., the first end 14 or the second end 16) of the expandable framework 12.

Figure 5B:
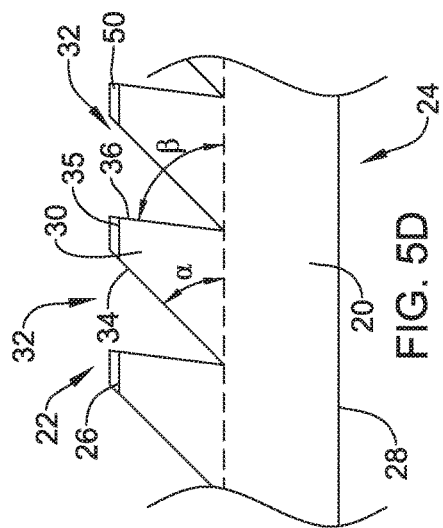

As shown in FIG. 5B, in some instances the angle $\alpha$ of the first flank 34 may be an acute angle such that the first flank 34 slopes radially outward from the longitudinal axis toward an end (e.g., the first end 14 or the second end 16) of the expandable framework 12 while the angle $\beta$ of the second flank 36 may be a perpendicular angle such that second flank 36 may extend perpendicular to the longitudinal axis of the expandable framework 12.

In other instances the angle α of the first flank 34 may be an acute angle such that the first flank 34 slopes radially outward from the longitudinal axis toward an end (e.g., the first end 14 or the second end 16) of the expandable framework 12 while the angle β of the second flank 36 may be an obtuse angle such that second flank 36 slopes radially outward from the longitudinal axis toward an opposite end (e.g., the second end 16 or the first end 14) of the expandable framework 12.

As illustrated in the embodiments of FIGS. 5A and 5B, in some instances the first flank 34 and the second flank 36 may converge to a point 38 along a line at a radially outwardmost extent of the anti-migration teeth 30. In some instances, the point 38 along the line may coincide with the radially outermost surface 26 of the expandable framework 12 on the radially outward face 22 of the expandable framework 12.

Figure 5C:
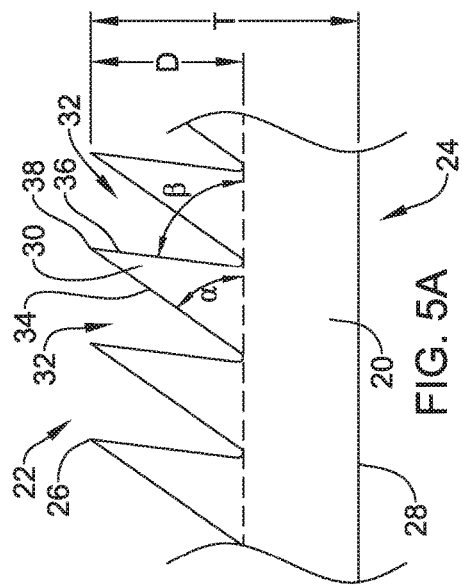

In other embodiments, such as shown in FIG. 5C, the anti-migration teeth 30 may include a surface, such as a flat surface 35, intersecting both the first flank 34 and the second flank 36. In some instances, the surface 35 may be generally parallel to the longitudinal axis X of the expandable framework 12. In other instances, the surface 35 may be oriented at an oblique angle to the longitudinal axis X of the expandable framework 12. In some instances, the surface 35 may be the radially outermost surface 26 of the expandable framework 12 on the radially outward face 22 of the expandable framework 12.

Figure 5D:
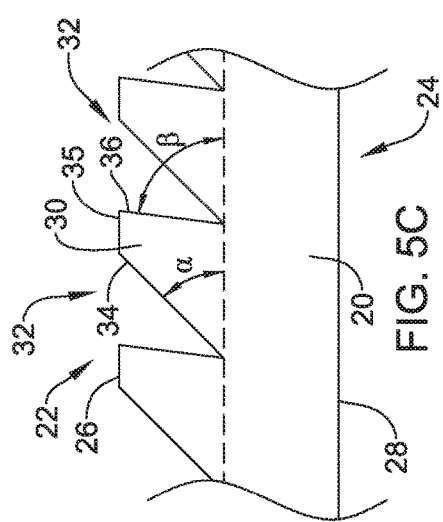

In some instances, the expandable framework 12 may include an outer covering 50, such as a polymeric coating, a polymeric sleeve, or other layer, overlying the radially outward surface 26 of the expandable framework 12. For example, as shown in FIG. 5D, the outer covering 50 may cover the surface 35 of the anti-migration teeth 30, or other portion of the radially outward surface 26 of the expandable framework 12. In some instances, the outer covering 50 may be applied to the radially outward surface 26 prior to the anti-migration grooves 32, defining the anti-migration teeth 30 therebetween, being formed in the expandable framework 12 (e.g., before the anti-migration grooves 32 and/or the interconnected struts 20 are cut out of the tubular member). Accordingly, the anti-migration grooves 32 between the anti-migration teeth 30 may be devoid of the covering 50. In other words, the covering 50 may not occupy the anti-migration grooves 32. In other instances, the covering 50 may be applied to the expandable framework 12 after the anti-migration grooves 32 may been formed.

Referring to FIG. 5A, in some instances, the base of an anti-migration groove 32, defined between the first flank 34 of a first tooth 30 and the second flank 36 of an adjacent second tooth 30 may be rounded (i.e., have a radius of curvature from the first flank 34 to the second flank 36. In other instances, such as shown in FIGS. 5B-5D, the base of an anti-migration groove 32, defined between the first flank 34 of a first tooth 30 and the second flank 36 of an adjacent second tooth 30 may be a sharp angle (i.e., the first flank 34 of a first tooth 30 and the second flank 36 of an adjacent second tooth 30 may intersect at an angle). It is noted that although only FIG. 5A illustrates a rounded base of the anti-migration groove 32, any of the other embodiments may also have anti-migration grooves 32 with a rounded base.

Depicted in FIG. 5A, yet equally applicable to the embodiments of FIGS. 5B-5D, the interconnected struts 20 of the expandable framework 12 may have a thickness T measured in a radial direction perpendicular to the longitudinal axis of the expandable framework 12. The thickness T is measured from the radially inward surface 28 on the radially inward face 24 of the interconnected struts 20 of the expandable framework 12 to the radially outward surface 26 (e.g., point 38 and/or surface 35) on the radially outward face 22 of the interconnected struts 20 of the expandable framework 12.

The anti-migration grooves 32 may extend into the struts 20 from the radially outward surface 26 on the radially outward face 22 of the interconnected struts 20 a depth D, which is measured parallel to the thickness T. The depth D may be less than the thickness T of the struts 20 such that the anti-migration grooves 32 do not extend entirely to the radially inward surface 28 on the radially inward face 24 of the interconnected struts 20. Accordingly, some material of the struts 20 may remain radially inward of the base of the anti-migration grooves 32. In some instances, the anti-migration grooves 32 may have a depth D of 1% to 25%, or about 1% to about 25%, 1% to 20%, or about 1% to about 20%, 1% to 10%, or about 1% to about 10%, 2% to 15%, or about 2% to about 15%, 2% to 10%, or about 2% to about 10%, 5% to 15%, or about 5% to about 15%, or 5% to 10%, or about 5% to about 10% of the thickness T of the struts 20.

Figure 6:
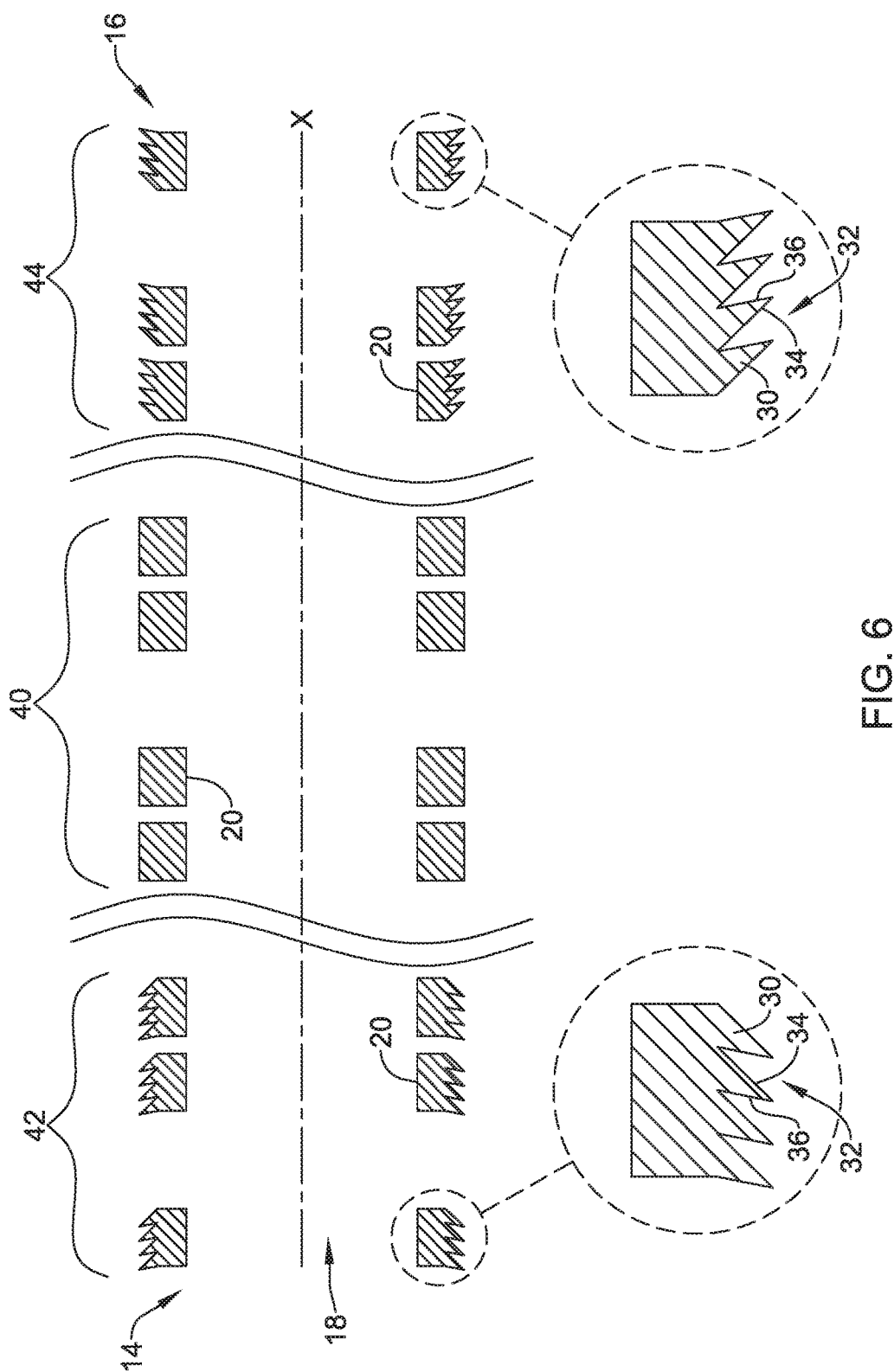
FIG. 6 is a longitudinal cross-section of an alternative configuration of the endoprosthesis of FIG. 1.

As shown in FIG. 6, in some instances, the expandable framework 12 may include a first end region 42 and a second end region 44, which are separated by an intermediate region 40. The first end region 42 may include the first end 14 and extend therefrom to the intermediate region 40. The second end region 44 may include the second end 16 and extend therefrom to the intermediate region 40. In other words, the first end region 42 may extend from the intermediate region 40 to or toward the first end 14, while the second end region 44 may extend from the intermediate region 40 to or toward the second end 16.

In some instances, a first portion of the anti-migration teeth 30 may include at least one of the first and second flanks 34, 36 angled toward the first end 14 of the expandable framework 12, and a second portion of the anti-migration teeth 30 may include at least one of the first and second flanks 34, 36 angled toward the second end 16. In some instances, as shown in FIG. 6, a first portion of the anti-migration teeth 30 may include both of the first and second flanks 34, 36 angled toward the first end 14 of the expandable framework 12, while a second portion of the anti-migration teeth 30 may include both of the first and second flanks 34, 36 angled toward the second end 16. In some instances, the first portion of anti-migration teeth 30 may be located proximate the first end 14 and the second portion of anti-migration teeth 30 may be located proximate the second end 16. For instance, the first end region 42 may include a first portion of the anti-migration teeth 30 which include at least one of the first and second flanks 34, 36 (or both of the first and second flanks 34) angled toward the first end 14 of the expandable framework 12. The second end region 44 may include a second portion of the anti-migration teeth 30 which include at least one of the first and second flanks 34, 36 (or both of the first and second flanks 34) angled toward the second end 16 of the expandable framework 12.

In other instances, the first end region 42 may include the second portion of the anti-migration teeth 30 which include at least one of the first and second flanks 34, 36 (or both of the first and second flanks 34) angled toward the second end 16 of the expandable framework 12. The second end region 44 may include the first portion of the anti-migration teeth 30 which include at least one of the first and second flanks 34, 36 (or both of the first and second flanks 34) angled toward the first end 14 of the expandable framework 12.

In some instances, a portion of the expandable framework 12 may be devoid of anti-migration teeth 30. For instance, as shown in FIG. 6, the intermediate region 40 of the expandable framework 12, between the first portion of anti-migration teeth 30 and the second portion of anti-migration teeth 30, may be devoid of anti-migration teeth.

The anti-migration teeth 30 may provide additional surface area to increase traction between the endoprosthesis 10 and the luminal surface of a body lumen within which the endoprosthesis 10 is implanted. Thus, the anti-migration teeth 30 may engage tissue to resist migration of the endoprosthesis 10 when implanted in a body lumen. For example, the endoprosthesis 10 may be implanted (e.g., expanded) within a body lumen such that the anti-migration teeth 30 engage the luminal surface of the body lumen. Any forces applied to the endoprosthesis 10 in a proximal and/or distal direction may be opposed by the engagement of the anti-migration teeth 30 with the luminal surface of the body lumen, preventing longitudinal movement (either proximally or distally) of the endoprosthesis 10 in the body lumen.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. An endoprosthesis comprising:
an expandable tubular framework having a first end, a second end, and a lumen extending therethrough along a longitudinal axis, the lumen defining an inner surface, the expandable tubular framework including a plurality of interconnected struts and openings extending between the inner surface and a radially outward surface of the interconnected struts, wherein an entirety of the expandable tubular framework is formed from a monolithic tubular member subsequent removal of material from the tubular member to form the openings;
wherein the radially outward surface of the interconnected struts includes a plurality of anti-migration grooves defining anti-migration teeth formed therebetween, wherein a portion of the interconnected struts is devoid of anti-migration teeth, the portion devoid of anti-migration teeth having a first thickness measured between the inner surface and the radially outward surface, wherein a point defining a radially outward-most extent of the anti-migration teeth is located on the radially outward surface of the interconnected struts such that a second thickness measured between the inner surface and the point defining the radially outward-most extent of the anti-migration teeth is the same as the first thickness;
wherein the anti-migration teeth are configured to engage tissue to resist migration of the endoprosthesis within a body lumen.

2. The endoprosthesis of claim 1, wherein each of the anti-migration teeth include a first flank and a second flank converging toward the first flank.

3. The endoprosthesis of claim 2, wherein the first flank slopes radially outward toward the first end at an acute angle with respect to the longitudinal axis.

4. The endoprosthesis of claim 3, wherein the second flank slopes radially outward toward the first end at an acute angle with respect to the longitudinal axis.

5. The endoprosthesis of claim 4, wherein the angle of the first flank is less than the angle of the second flank.

6. The endoprosthesis of claim 2, wherein the first flank and the second flank converge to a point along a line.

7. The endoprosthesis of claim 2, wherein the anti-migration teeth further include a flat surface intersecting both the first flank and the second flank.

8. The endoprosthesis of claim 2, wherein a first portion of the anti-migration teeth include at least one of the first and second flanks angled toward the first end, and a second portion of the anti-migration teeth include at least one of the first and second flanks angled toward the second end.

9. The endoprosthesis of claim 8, wherein the first portion of the anti-migration teeth are located proximate the first end and the second portion of the anti-migration teeth are located proximate the second end.

10. The endoprosthesis of claim 8, wherein the first portion of the anti-migration teeth are located proximate the second end and the second portion of the anti-migration teeth are located proximate the first end.

11. The endoprosthesis of claim 8, wherein the expandable tubular framework is devoid of anti-migration teeth between the first portion of anti-migration teeth and the second portion of anti-migration teeth.

12. An endoprosthesis comprising:
an expandable tubular framework having a first end, a second end, and a lumen extending therethrough along a longitudinal axis, the lumen defining an inner surface, the expandable tubular framework including a plurality of interconnected struts and openings extending between the inner surface and a radially outward surface of the interconnected struts, wherein an entirety of the expandable tubular framework is formed from a monolithic tubular member subsequent removal of material from the tubular member;
wherein the radially outward surface includes a plurality of anti-migration grooves cut into the radially outward surface of the interconnected struts to define anti-migration teeth formed therebetween;
wherein the anti-migration teeth include a first flank and a second flank converging toward the first flank, wherein the second flank of a first anti-migration tooth meets the first flank of an adjacent second anti-migration tooth at a point defining a lower end of the groove between the first and second teeth;
wherein a first portion of the anti-migration teeth adjacent the first end of the expandable tubular framework are angled in a first direction and a second portion of the anti-migration teeth adjacent the second end of the expandable tubular framework are angled in a second direction opposite the first direction;
wherein the anti-migration teeth are configured to engage tissue to resist migration of the endoprosthesis within a body lumen.

13. The endoprosthesis of claim 12, wherein the first portion of the anti-migration teeth include the first and second flanks angled toward the first end, and the second portion of the anti-migration teeth include the first and second flanks angled toward the second end.

14. The endoprosthesis of claim 12, wherein the first flank of the first portion of the anti-migration teeth slopes radially outward toward the first end at a first acute angle with respect to the longitudinal axis and the first flank of the second portion of the anti-migration teeth slopes radially outward toward the second end at the first acute angle with respect to the longitudinal axis.

15. The endoprosthesis of claim 14, wherein the second flank of the first portion of the anti-migration teeth slopes radially outward toward the first end at a second acute angle with respect to the longitudinal axis and the second flank of the second portion of the anti-migration teeth slopes radially outward toward the second end at the second acute angle with respect to the longitudinal axis.

16. The endoprosthesis of claim 15, wherein the first acute angle is less than the second acute angle.

17. The endoprosthesis of claim 12, wherein the anti-migration teeth further include a flat surface intersecting both the first flank and the second flank.

18. A method of forming an endoprosthesis, comprising:
forming an expandable tubular framework from a monolithic tubular member, the expandable tubular framework having a first end, a second end, and a lumen extending therethrough along a longitudinal axis, the lumen defining an inner surface, the expandable tubular framework including a plurality of interconnected struts and openings extending between the inner surface and a radially outward surface of the interconnected struts, wherein an entirety of the expandable tubular framework is formed from the monolithic tubular member subsequent removal of material from the tubular member; and
forming a plurality of anti-migration grooves in the radially outward facing surface, thereby defining a plurality of anti-migration teeth between adjacent anti-migration grooves, wherein a portion of the interconnected struts is devoid of anti-migration teeth, the portion devoid of anti-migration teeth having a first thickness measured between the inner surface and the radially outward facing surface, wherein a point defining a radially outward-most extent of the anti-migration teeth is located on the radially outward surface of the interconnected struts such that a second thickness measured between the inner surface and the point defining the radially outward-most extent of the anti-migration teeth is the same as the first thickness.

19. The method of claim 18, wherein:
the anti-migration teeth include a first flank and a second flank converging toward the first flank;
the first flank slopes radially outward toward the first end at an acute angle from the longitudinal axis;
the second flank slopes radially outward toward the first end at an acute angle from the longitudinal axis; and
the angle of the first flank is less than the angle of the second flank.

20. The method of claim 18, wherein the anti-migration teeth further include a flat surface intersecting both the first flank and the second flank.

* * * * *